(12) United States Patent
Biedermann et al.

(10) Patent No.: US 11,937,850 B2
(45) Date of Patent: Mar. 26, 2024

(54) POLYAXIAL BONE ANCHORING DEVICE AND SYSTEM INCLUDING AN INSTRUMENT AND A POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: BIEDERMANN TECHNOLOGIES & CO. KG, Donaueschingen (DE)

( * ) Notice: Subject to any disclaimer, the term of this patent is extended or adjusted under 35 U.S.C. 154(b) by 0 days.

(21) Appl. No.: 17/190,937

(22) Filed: Mar. 3, 2021

(65) Prior Publication Data

US 2021/0259743 A1   Aug. 26, 2021

Related U.S. Application Data

(63) Continuation of application No. 16/224,535, filed on Dec. 18, 2018, now Pat. No. 10,973,554.
(Continued)

(30) Foreign Application Priority Data

Dec. 22, 2017   (EP) .................................. 17210500

(51) Int. Cl.
*A61B 17/70*   (2006.01)
(52) U.S. Cl.
CPC ...... *A61B 17/7037* (2013.01); *A61B 17/7032* (2013.01); *A61B 17/7035* (2013.01)

(58) Field of Classification Search
None
See application file for complete search history.

(56) References Cited

U.S. PATENT DOCUMENTS

| | | | |
|---|---|---|---|
| 5,549,608 | A | 8/1996 | Errico et al. |
| 2007/0173819 | A1 | 7/2007 | Sandlin |

(Continued)

FOREIGN PATENT DOCUMENTS

| | | |
|---|---|---|
| CN | 103976785 A | 8/2014 |
| EP | 2 682 062 A1 | 1/2014 |
| WO | WO 2016/170452 A1 | 10/2016 |

OTHER PUBLICATIONS

Extended European Search Report for Application No. 17210500.9, dated Jun. 28, 2018, 8 pages.

*Primary Examiner* — Tessa M Matthews
(74) *Attorney, Agent, or Firm* — Lewis Roca Rothgerber Christie LLP

(57) ABSTRACT

A bone anchoring device includes a receiving part having a central axis, two legs defining a recess for receiving a rod, and a head receiving portion that is at least partially expandable and having an opening for inserting and pivotably holding a head of a bone anchoring element therein, and a locking ring mountable around the head receiving portion in an axial direction while a rotational orientation of the locking ring relative to the receiving part remains constant. When the locking ring is around the head receiving portion, the locking ring is rotatable around the central axis from a first rotational orientation to a second rotational orientation where a compressive force exerted by the locking ring on the head receiving portion is greater than at the first rotational orientation.

20 Claims, 12 Drawing Sheets

Related U.S. Application Data

(60) Provisional application No. 62/609,862, filed on Dec. 22, 2017.

(56) References Cited

U.S. PATENT DOCUMENTS

| | | |
|---|---|---|
| 2008/0015576 A1 | 1/2008 | Whipple |
| 2009/0036934 A1 | 2/2009 | Biedermann et al. |
| 2009/0149887 A1 | 6/2009 | Schlaepfer et al. |
| 2014/0012337 A1* | 1/2014 | Biedermann ........ A61B 17/844 606/328 |
| 2014/0031880 A1* | 1/2014 | Biedermann ...... A61B 17/7035 606/305 |
| 2014/0214084 A1* | 7/2014 | Jackson ............. A61B 17/7037 606/267 |
| 2014/0214097 A1 | 7/2014 | Jackson et al. |
| 2014/0236239 A1 | 8/2014 | Biedermann et al. |
| 2016/0331412 A1* | 11/2016 | Biedermann ...... A61B 17/7037 |
| 2017/0020574 A1 | 1/2017 | Biedermann et al. |
| 2018/0055542 A1 | 3/2018 | Biedermann |

* cited by examiner

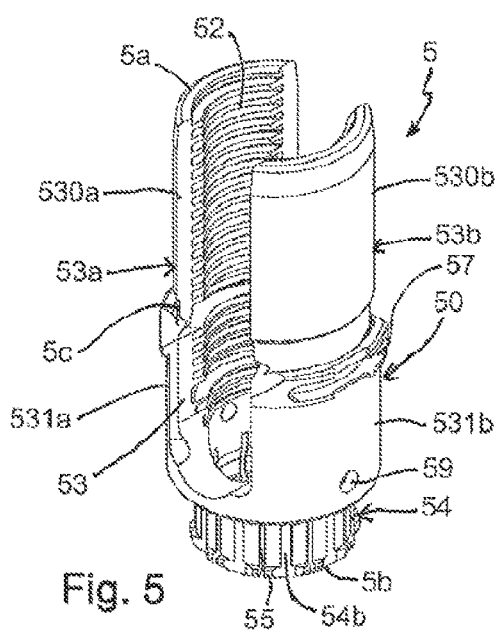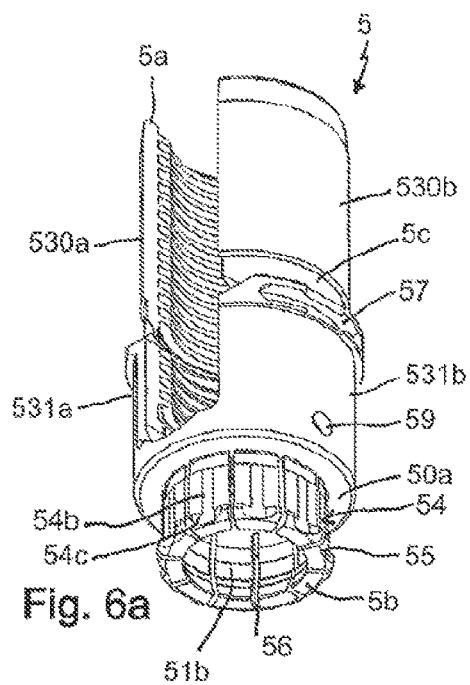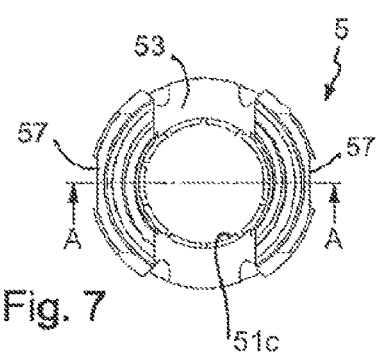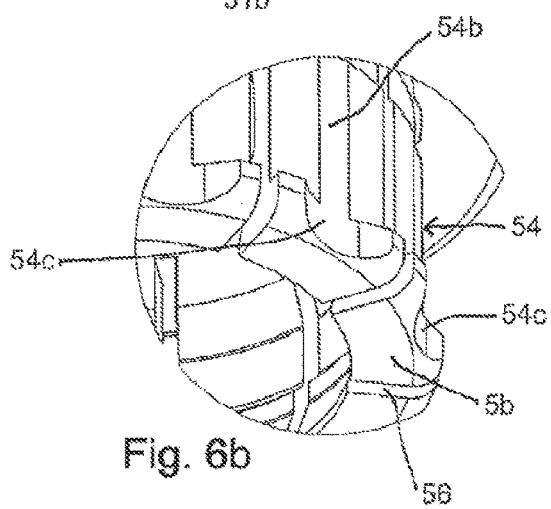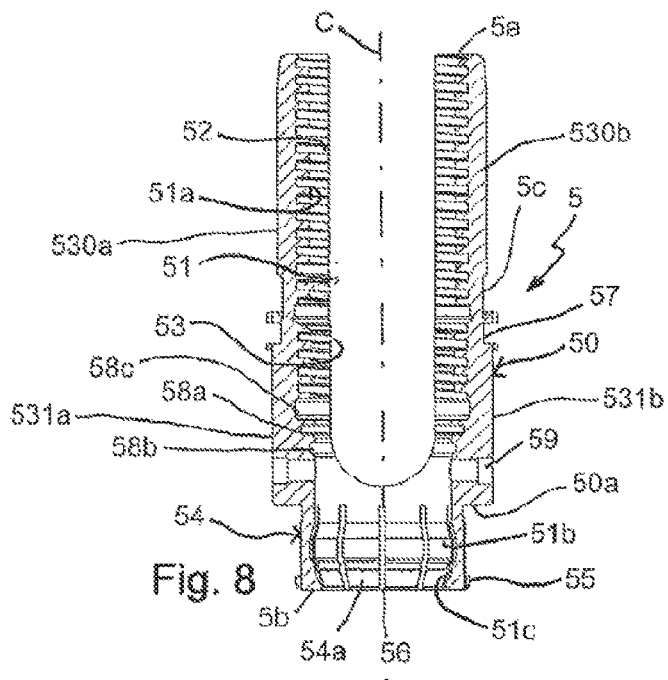

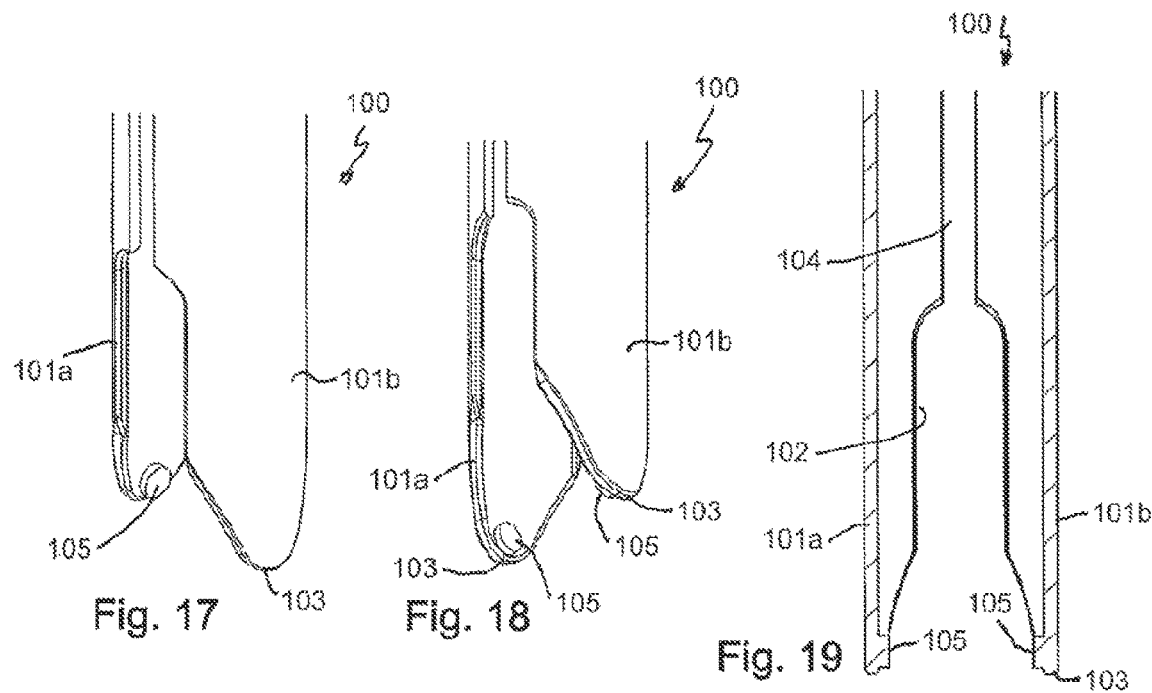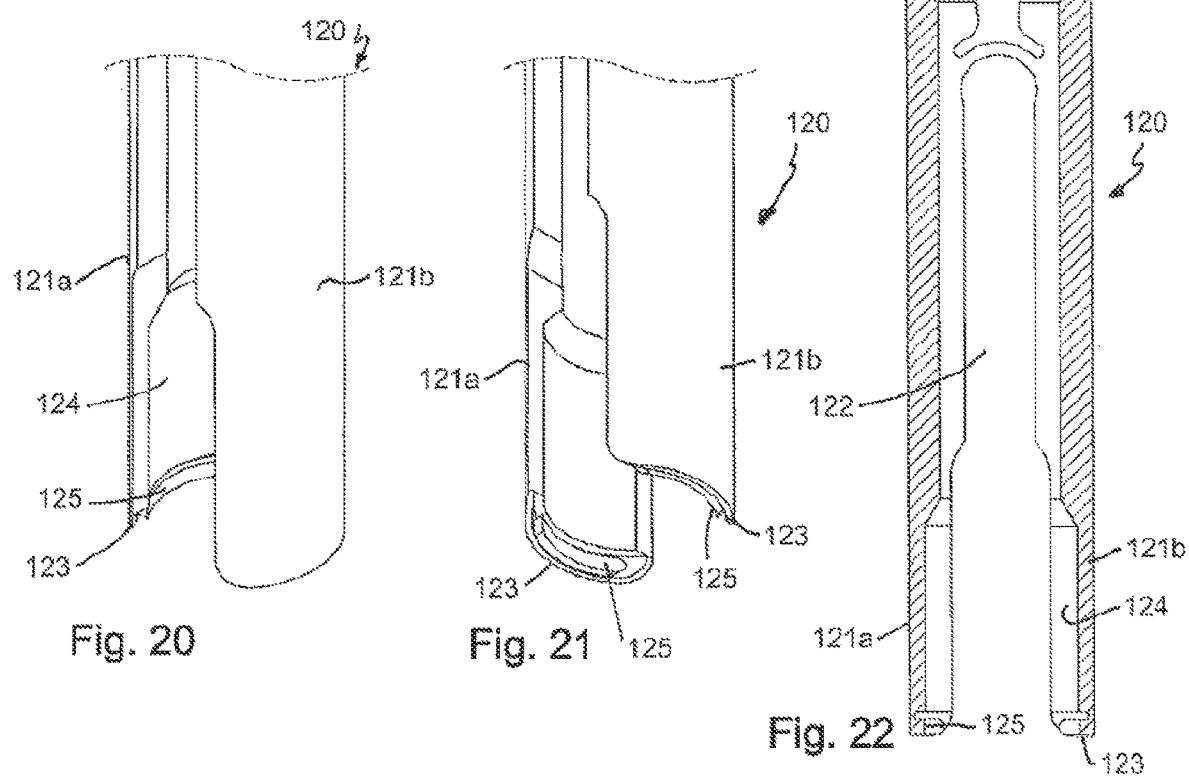

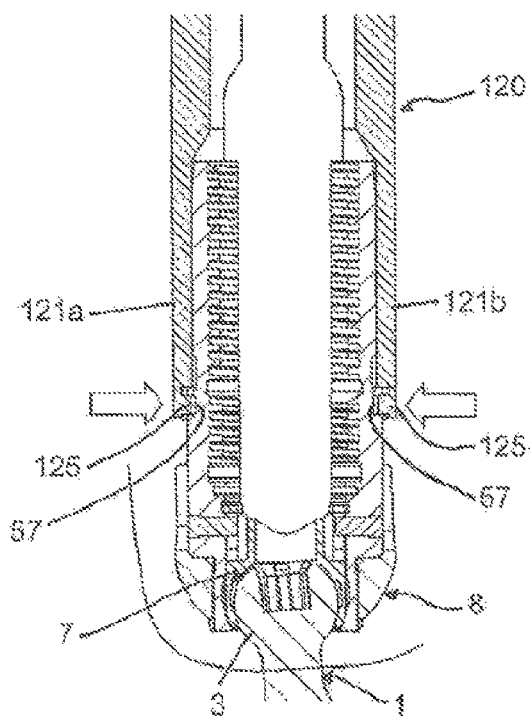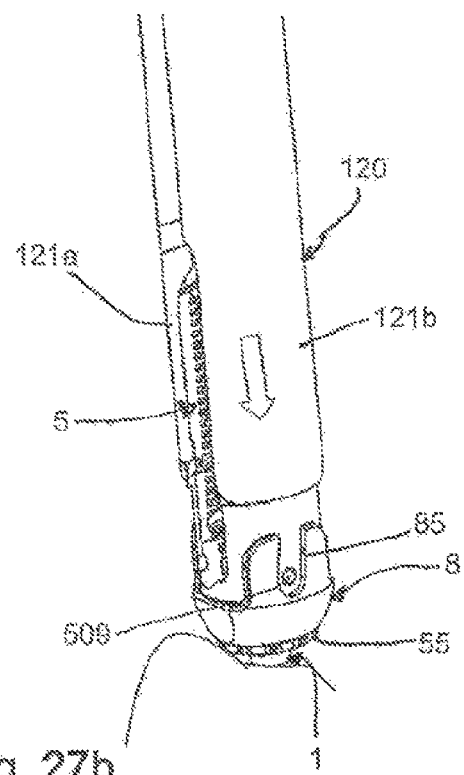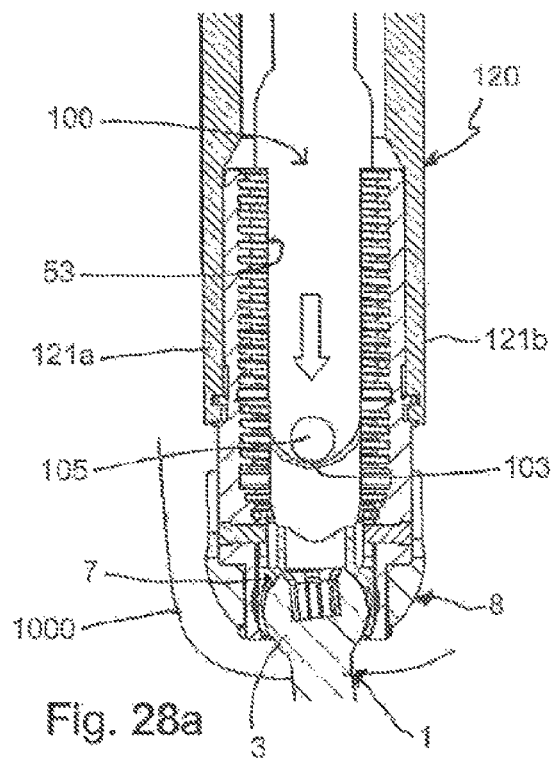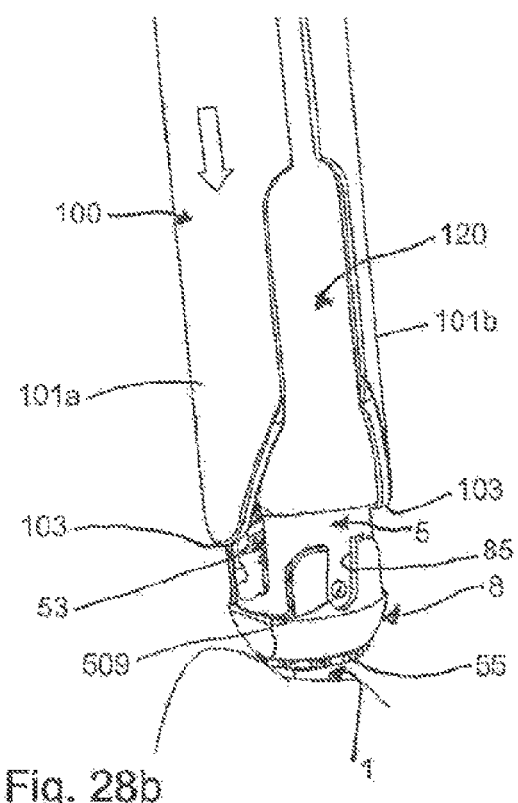

POLYAXIAL BONE ANCHORING DEVICE AND SYSTEM INCLUDING AN INSTRUMENT AND A POLYAXIAL BONE ANCHORING DEVICE

CROSS-REFERENCE TO RELATED APPLICATION(S)

This application is a continuation of U.S. patent application Ser. No. 16/224,535, filed Dec. 18, 2018, which claims priority to and the benefit of U.S. Provisional Patent Application No. 62/609,862, filed Dec. 22, 2017, the contents of both of which are hereby incorporated by reference in their entirety, and claims priority from European Patent Application EP 17 210 500.9, filed Dec. 22, 2017, the contents of which are hereby incorporated by reference in their entirety.

BACKGROUND

The invention relates to a polyaxial bone anchoring device and a system including a polyaxial bone anchoring device and an instrument for use with the device. More specifically, the bone anchoring device includes a receiving part for coupling a rod to a bone anchoring element and a locking ring for locking a head of the bone anchoring element and for releasing the locking, for example via the instrument.

DESCRIPTION OF RELATED ART

A polyaxial bone anchoring device of this type is known from US 2017/0020574 A1. The known polyaxial bone anchoring device includes a receiving part with a rod receiving portion and a flexible head receiving portion for inserting and clamping a head of a bone anchoring element. Further, a locking ring is provided that is configured to be arranged around the head receiving portion for locking the head. The receiving part includes a first engagement structure and the locking ring includes a second engagement structure, wherein the engagement structures are configured to be engaged by an instrument to move the locking relative to the receiving part along a central axis from a locking position towards a position where the inserted head is pivotable.

US 2016/0331412 A1 describes a coupling device for coupling a rod to a bone anchoring element, wherein the coupling device includes a receiving part that defines an accommodation space for accommodating a head of the bone anchoring element. The coupling device further includes a pressure element arranged at least partially in the accommodation space, the pressure element having a flexible portion to clamp an inserted head, and a clamping element extending at least partially around the flexible portion of the pressure element. The clamping element is configured to move from a first position to a second position in which the clamping element exerts a clamping force onto the pressure element, where the movement includes rotating the clamping element around a central axis.

WO 2016/170452 A1 describes vertebral osteosynthesis equipment including at least one connecting bar and at least one anchor member of the "tulip" type and of the so-called "polyaxial" type. The anchor member includes a body and a head that forms an engagement duct for the connecting bar wherein said head is articulated relative to said body. The anchor member further includes a ring being angularly mobile relative to the head. The ring can assume a first position along the axis of the head in which the head is movable in an articulated manner relative to the body and a second position along the axis of the head in which the head is made immobile or substantially immobile relative to the body.

SUMMARY

In spinal surgery, often multiple segments of the spinal column have to be corrected and/or stabilized using a spinal rod and polyaxial bone anchors. During such a procedure, repeated adjustments of a bone anchoring element and the rod relative to a receiving part of a polyaxial bone anchoring device may become necessary.

It is therefore an object of the invention to provide a further improved polyaxial bone anchoring device that allows for safe and convenient handling during surgery, and to provide a system including such a polyaxial bone anchoring device and an instrument adapted for use therewith.

The bone anchoring element can be locked relative to the receiving part in an angular position and can be unlocked from that angular position independently from the fixation of the rod. Hence, the locking of the head can be maintained while adjustments to the position of the rod can be made.

The locking of the head is effected by rotating the locking ring in one direction around the central axis, and the unlocking is effected by rotating the locking ring in the opposite direction. With such a design, the size of a head receiving portion of the receiving part may be reduced in an axial direction to achieve a low profile. A further clinical advantage may be that the exertion of pressure onto the vertebrae when locking the head can be reduced as it is not necessary to move the locking ring downward for locking the head. Moreover, the unlocking requires less force compared to known devices in which the locking is achieved through engagement of two tapered surfaces of the locking ring and the head receiving portion, respectively.

The locking and unlocking of the bone anchoring device during surgery can also be carried out with the rod not yet inserted or being at an elevated position in the receiving part, away from the bottom of a rod receiving recess. This increases the possibilities of carrying out correction steps during surgery.

If additionally, a pressure member is provided for exerting pressure onto the head, the clamping force may be distributed onto the head more effectively. Moreover, when locking the rod, pressure exerted by the rod onto the pressure member may further increase the locking force onto the head.

The legs may each have a separable portion that forms extended tabs. The extended tabs allow convenient manipulation of the polyaxial bone anchoring device during surgery. Furthermore, the extended tabs permit guiding and/or supplying elements of an implant or instruments to the implantation site. This is particularly useful in the case of minimally invasive surgery (MIS). The extended tabs may be broken off after locking the head and the rod.

The instrument is convenient to operate, as a downward movement is associated with locking of the head, and an upward movement is associated with unlocking of the head in the receiving part. Moreover, the instrument can be used even if the rod and the fixation element are already inserted into the channel of the receiving part but the rod is not yet fixed. Thus, a temporary locking of the bone anchoring element in the receiving part can be achieved with the instrument. When the head of the bone anchoring element is locked in the receiving part and the rod is still movable, it is possible to pull the bone anchoring device with the instrument towards the inserted rod, thereby also pulling the associated vertebra towards the rod for correcting a position of the vertebra. Therefore, the polyaxial bone anchoring device permits various adjustments and re-adjustments of the angular position and/or rod position during surgery.

The polyaxial bone anchoring device may be used as a bottom loading bone anchoring device in such a manner that the bone anchoring element is first inserted into the bone, and thereafter the receiving part with the locking ring is mounted onto the head of the bone anchoring element. Moreover, with a polyaxial bone anchoring device, a modular system may be provided that allows combining of various anchoring elements with the receiving part on demand, depending on the actual clinical requirements. This reduces the overall costs of using polyaxial screws, reduces the inventory, and gives the surgeon a wider or more versatile choice of implants.

BRIEF DESCRIPTION OF THE DRAWINGS

Further features and advantages of the invention will become apparent from the description of embodiments by means of the accompanying drawings. In the drawings:

FIG. 5 shows a perspective view from a top of a receiving part of the polyaxial bone anchoring device of FIGS. 1 to 4.

FIG. 6a shows a perspective view from a bottom of the receiving part of FIG. 5.

FIG. 6b shows an enlarged view of a detail of FIG. 6a.

FIG. 7 shows a top view of the receiving part of FIGS. 5, 6a, and 6b.

FIG. 8 shows a cross-sectional view of the receiving of FIGS. 5 to 7, the cross-section taken along line A-A in FIG. 7.

FIG. 17 shows a perspective view from a side of a front portion of an outer tube of an instrument for use with the polyaxial bone anchoring device of FIGS. 1 to 4.

FIG. 18 shows a perspective view from a bottom of the front portion of the outer tube of FIG. 17.

FIG. 19 shows a cross-sectional view of the front portion of the outer tube of FIGS. 17 and 18, wherein the cross-section is taken in a plane extending through a central longitudinal axis of the outer tube and through centers of opposed arms of the outer tube.

FIG. 20 shows a perspective view from a side of a front portion of an inner tube of the instrument for use with the polyaxial bone anchoring device of FIGS. 1 to 4.

FIG. 21 shows a perspective view from a bottom of the front portion of the inner tube of FIG. 20.

FIG. 22 shows a cross-sectional view of the front portion of the inner tube of the instrument as shown in FIGS. 20 and 21, wherein the cross-section is taken in a plane extending through a central longitudinal axis of the instrument and through centers of arms of the inner tube.

FIGS. 27a and 27b show a cross-sectional view and a perspective view, respectively, of the polyaxial bone anchoring device of FIG. 26, with the inner tube of the instrument fixed to the receiving part.

FIGS. 28a and 28b show a cross-sectional view and a perspective view, respectively, of the polyaxial bone anchoring device of FIGS. 27a and 27b, and after a first step of mounting the outer tube of the instrument.

DETAILED DESCRIPTION

Figures 1, 2:
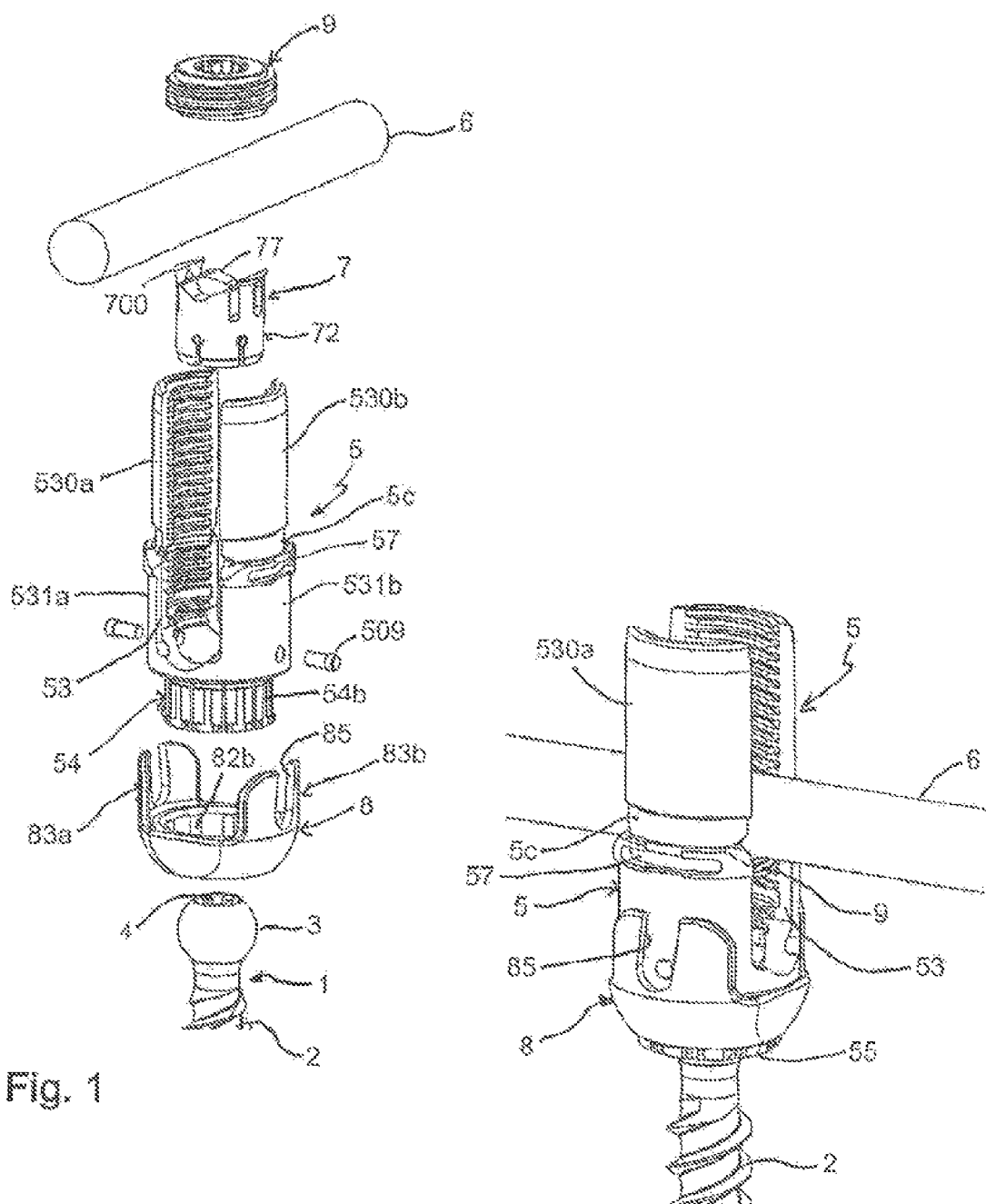
FIG. 1 shows an exploded perspective view of an embodiment of a polyaxial bone anchoring device.
FIG. 2 shows a perspective view of the polyaxial bone anchoring device of FIG. 1 in an assembled state.

As shown in FIGS. 1 to 4, a polyaxial bone anchoring device according to an embodiment of the invention includes a bone anchoring element 1 in the form of, for example, a bone screw having a shank 2 with a threaded portion and a head 3 with a spherically-shaped outer surface portion. The head 3 may have a recess 4 for engagement with a driver. The bone anchoring device also includes a receiving part 5 for receiving a rod 6 to be connected to the bone anchoring element 1. In addition, a pressure member 7 may be provided in the receiving part 5 for exerting pressure onto the head 3 of the bone anchoring element 1. Further, the bone anchoring device includes a locking ring 8 that is mountable to the receiving part 5 for compressing a portion of the receiving part 5 to exert pressure onto the head 3. Lastly, the bone anchoring device also includes a fixation element 9, in the form of, for example, an inner screw or set screw for fixing the rod in the receiving part 5.

The receiving part 5 will be described in greater detail, referring additionally to FIGS. 5 to 8. The receiving part 5 includes an upper or first end 5a and an opposite lower or second end 5b, and a central axis C that passes through the first end 5a and the second end 5b. A passage 51 extends through the receiving part 5 from the first end 5a to the second end 5b. The passage 51 may have several sections having different diameters. In one section that starts at the first end 5a and extends to a distance from the first end 5a, the passage 51 is formed as a coaxial bore 51a that may be provided at least in a portion thereof with an internal thread 52. The passage 51 further may widen into an accommodation space 51b that serves for accommodating the head 3 of the bone anchoring element and at least a portion of the pressure member 7. At or close to the second end 5b, the accommodation space 51b narrows in a narrowing portion 51c that narrows towards the second end 5b. The narrowing portion 51c can be tapered, more specifically, conically tapered, or can narrow in another shape. The opening defined by the passage 51 at the second end 5b is configured to let the head 3 of the bone anchoring element 1 pass therethrough, so that the bone anchoring device can be used as a bottom loading polyaxial bone anchoring device.

A recess 53 that may be substantially U-shaped extends from the first end 5a in the direction of the second end 5b, wherein a width of the recess 53 is slightly larger than a diameter of the rod 6, such that the rod 6 can be placed in the recess 53 and can be guided therein. By means of this, the recess 53 forms a rod receiving recess or a channel for the rod 6. By means of the recess 53, two free legs 53a, 53b are formed, on which the internal thread 52 is at least partially located. The internal thread 52 can be, for example, a metric thread, a flat thread, a negative angle-thread, a saw-tooth thread, or any other thread form. Preferably, a thread form such as a flat thread or a negative angle thread is used to prevent or reduce splaying of the legs 53a, 53b when the fixation element 9 is screwed in.

At a distance from the first end 5a, a weakened section that permits breaking away or breaking off of a portion of the legs 53a, 53b is provided. The weakened section includes a circumferential groove 5c on the outer surface of the receiving part 5 that divides legs 53a, 53b into a first or upper portion 530a, 530b extending above the groove 5c, and a second or lower portion 531a, 531b extending below the groove 5c to a base of the recess 53. At the groove 5c, the wall thickness of the legs 53a, 53b is reduced. By means of this, the upper portions 530a, 530b, respectively, form extended legs, also called extended tabs, of the bone anchoring device. Such extended tabs may be particularly suitable to define a pathway, for example in minimally invasive surgery (MIS), to guide an implant component, for example the rod 6 or the fixation element 9, to the bone anchoring element 1 at the implantation site beneath the skin of the patient. Any other means for providing a weakened section for permitting breaking away of the upper portion 530a, 530b from the lower portion 531a, 531b may be contemplated, such as, for example, perforations, etc.

The internal thread 52 is provided along at least part of the upper portion 530a, 530b, and along at least part of the lower portion 531a, 531b of the legs 53a, 53b, so that the fixation element 9 can be screwed down along the pathway defined by the coaxial bore 51a. The depth of the recess 53 is such that when the rod 6 is placed into the recess 53 and the fixation element 9 is screwed between the legs 53a, 53b, the fixation element 9 does not substantially protrude out of the receiving part 5 when the upper portions 530a, 530b of the legs have been broken off.

An upper part 50 of the receiving part 5, which includes the legs 53a, 53b forms a rod receiving portion of the receiving part. Between the upper part 50 and a second end 5b of the receiving part 5, a head receiving portion 54 of the receiving part 5 is provided that includes the accommodation space 51b. A greatest outer width of the head receiving portion 54 is smaller than a width of the receiving part 5 at a lower end 50a of the upper part 50, so that the lower end 50a of the rod receiving portion form a shoulder. The head receiving portion 54 has a substantially cylindrical outer surface portion with an outwardly protruding rim 55 at the second end 5b. The outwardly protruding rim 55 forms a stop for the locking ring 8, so that the locking ring 8, once mounted onto the receiving part 5, cannot be removed inadvertently. Moreover, an axial length of the cylindrical portion of the head receiving portion 54 corresponds substantially to a height of a main part of the locking ring 8, so that the locking ring 8, once mounted in practice, cannot move in an axial direction.

The head receiving portion 54 is flexible. In particular, it is compressible upon action of a force that is directed towards the central axis C. In the embodiment shown, the head receiving portion 54 includes a plurality of flexible wall sections 54a that are separated by slits 56 extending substantially parallel to the central axis C and being open towards the second end 5b. The number and size of the slits 56 is selected depending on the desired flexibility of the head receiving portion 54. Due to the flexibility of the head receiving portion 54, the opening at the second end 5b can also be expanded and compressed. More in detail, the size of the opening is such that the flexible wall sections 54a are spread apart when the head 3 enters and elastically snap back.

Referring now more in detail to FIGS. 6a and 6b, on the outer surface of preferably each of the flexible wall sections 54a, a longitudinally extending groove 54b is provided. The groove 54b runs preferably parallel to the central axis C and is located preferably in the center of the flexible wall section 54a, as seen in the circumferential direction around the central axis C. The grooves 54b serve for cooperating with a portion of the locking ring 8 described below. On the protruding outer rim 55, the grooves 54b are widened in a circumferential direction to form widened portions 54c. These widened portions 54c may facilitate the mounting of the locking ring 8. It shall be noted that while in the embodiment, each flexible wall section 54a has a groove 54b, it is sufficient that at least one or a reduced number, for example every other, flexible wall section 54a has such a groove 54b, to permit the locking ring 8 to exert pressure onto the head 3 and/or the pressure member 7 when the locking ring 8 is rotated. The grooves 54b may be shallow and may have a cylinder-segment shaped cross-section, but can also have any other cross-section that permits catching and releasing of a corresponding structure provided at the locking ring 8.

The outer surface of the upper part 50 is substantially cylindrical. In the region of the upper portion 530a, 530b of the legs, the outer diameter may be smaller than in a region adjacent to the lower end 50a of the upper part 50. Below the groove 5c, on each leg, a circumferentially extending engagement recess 57 is provided on the outer surface of the upper part 50. The engagement recess 57 serves for engagement with an instrument, more particularly with an inner tube of the instrument. Preferably, the engagement recesses end at a distance from the U-shaped recess 53 on each side.

Lastly, on the inner wall of the passage 51, two stops are provided for the pressure member. A first stop is formed by an upper wall of a first circumferential groove 58a located below the internal thread 52. The first stop prevents an upward movement of the pressure member 7 when the head 3 is inserted. A second stop is provided by a second circumferential groove 58b located at a distance from the first groove 58a in the direction towards the second end 5b. The second stop prevents upward movement of the pressure member 7 when the pressure member 7 is in a lower position, notably in a pre-locking position as described in more detail below. Additionally, an undercut 58c may be provided at a lower end of the internal thread 52.

Furthermore, in the wall of the receiving part 5, more specifically, in the wall of the upper part 50, at least one, preferably two holes 59 may be provided that may serve for inserting securing members, such as pins 509, to engage the pressure member 7. The holes 59 may be located at substantially 90° from the rod receiving recess 53 and diametrically opposite to each other.

The locking ring 8 will be described in greater detail, referring additionally to FIGS. 9 to 12. The locking ring 8 has an upper end or first end 8a and an opposite lower end or second end 8b, and may have a substantially spherical outer surface 81 between the first end 8a and the second end 8b that narrows towards the second end 8b. The outer diameter of the spherical surface 81 at or adjacent to the first end 8a may be such that when the locking ring 8 is mounted around the head receiving portion 54 of the receiving part 5, the locking ring does not substantially protrude outward from the upper part 50 of the receiving part 5, to ensure a compact design. It shall be noted, however, that the shape of the outer surface 81 of the locking ring 8 may be different in other embodiments. For example, the outer surface 81 may have a cylindrical or other shape. An axial height of the locking ring between the first end 8a and the second end 8b is such that the clamping ring fits onto the head receiving portion 54 of the receiving part 5 between the lower end 50a of the upper part 50 and the outwardly protruding rim 55.

Figure 12:
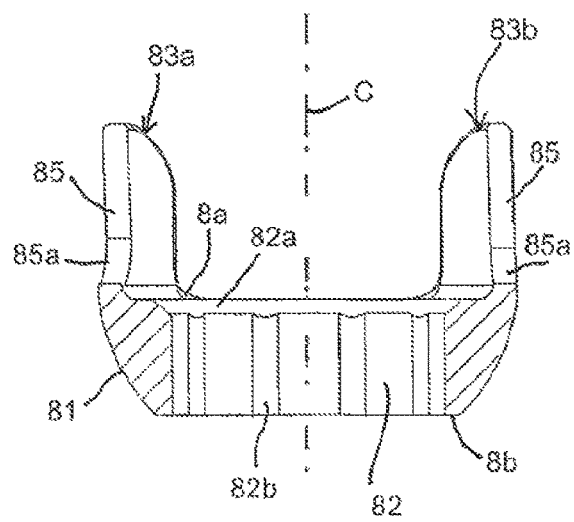
FIG. 12 shows a cross-sectional view of the locking ring of FIGS. 9 to 11, the cross-section taken along line B-B in FIG. 11.
Figure 13:
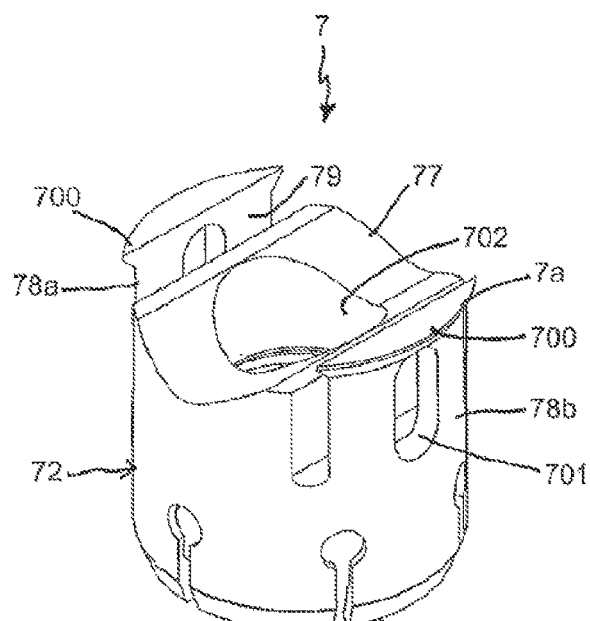
FIG. 13 shows a perspective view from a top of a pressure member of the polyaxial bone anchoring device of FIGS. 1 to 4.
Figure 14:
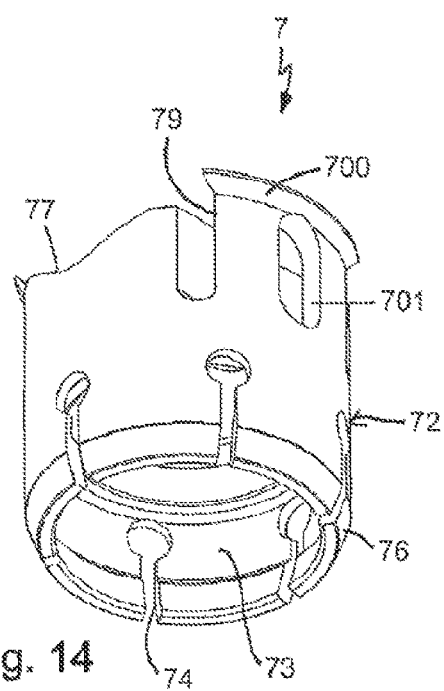
FIG. 14 shows a perspective view from a bottom of the pressure member of FIG. 13.
Figure 15:
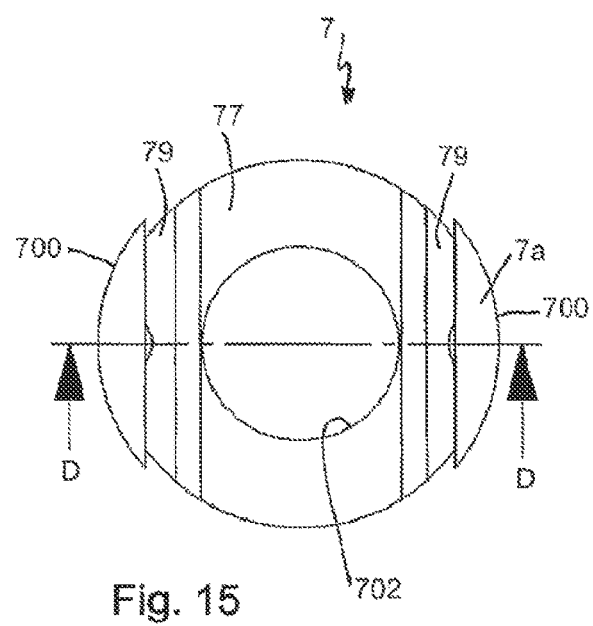
FIG. 15 shows a top view of the pressure member of FIGS. 13 and 14.
Figure 16:
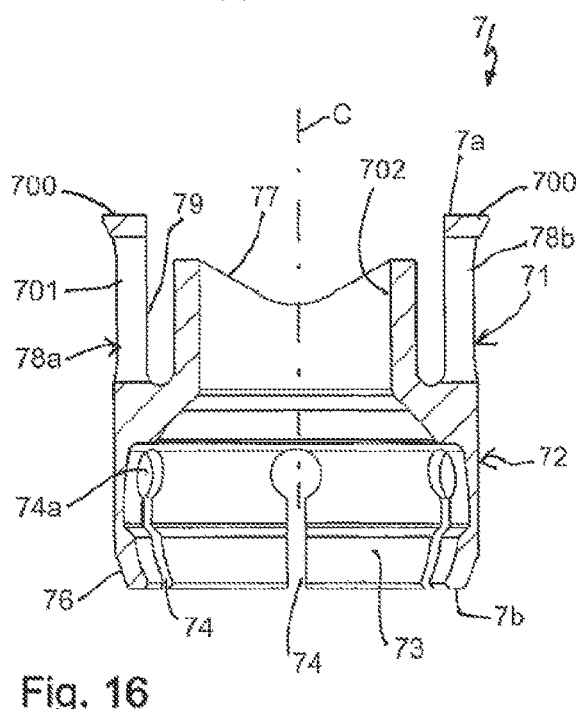
FIG. 16 shows a cross-sectional view of the pressure member of FIGS. 13 to 15, the cross-section taken along line D-D in FIG. 15.

As can be seen in particular in FIG. 12, the locking ring 8 has an inner cylindrical surface portion 82 that is adjacent to or substantially adjacent to the upper end 8a. On the inner cylindrical surface 82, a plurality of longitudinal protrusions or bulges 82b are formed that extend in an axial direction parallel to the central axis C when the locking ring 8 is mounted to the receiving part 5. The bulges 82b are spaced equidistantly in a circumferential direction. Their circumferential width is such that the bulges 82b are configured to engage the grooves 54b of the flexible wall portions 54a of the head receiving portion 54. The number of bulges 82b preferably corresponds to the number of grooves 54b of the head receiving portion 54.

Between the cylindrical inner surface portion 82 and the upper end, a small tapered section 82a may be provided that widens from the cylindrical inner surface portion 82 towards the first end 8a. This tapered portion 82a facilitates mounting of the locking ring 8 onto the head receiving portion 54.

The locking ring 8 further includes two upwardly projecting arms 83a, 83b extending from the first end 8a and having a free end 84. The free end 84 of the arms may be rounded at the edges. On each of the arms 83a, 83b, a notch 85 is formed that extends from the free end 84 of the arms to or close to the first end 8a. The notch 85 runs in a inclined manner relative to a line parallel to the central axis C when the locking ring 8 is mounted to the receiving part 5. As can be seen in particular in FIG. 9, the inclination of the grooves or notches 85 on the arms 83a, 83b is in the opposite direction with respect to each other when seen in a direction perpendicular to the central axis C, which is the rotation axis of the locking ring. A bottom 85a of the notch 85 may be rounded and a width of the notch 85 is such that a protrusion provided on the instrument, more specifically on an outer tube of the instrument, fits into the notch in a guiding manner. More in detail, when such a protrusion enters the notch 85, the protrusion is guided therein similar to the guiding function of a slotted link. An angle of inclination is selected such that by the guidance of the protrusion of the instrument, a suitable rotation of the locking ring 8 can be achieved.

Figure 24:
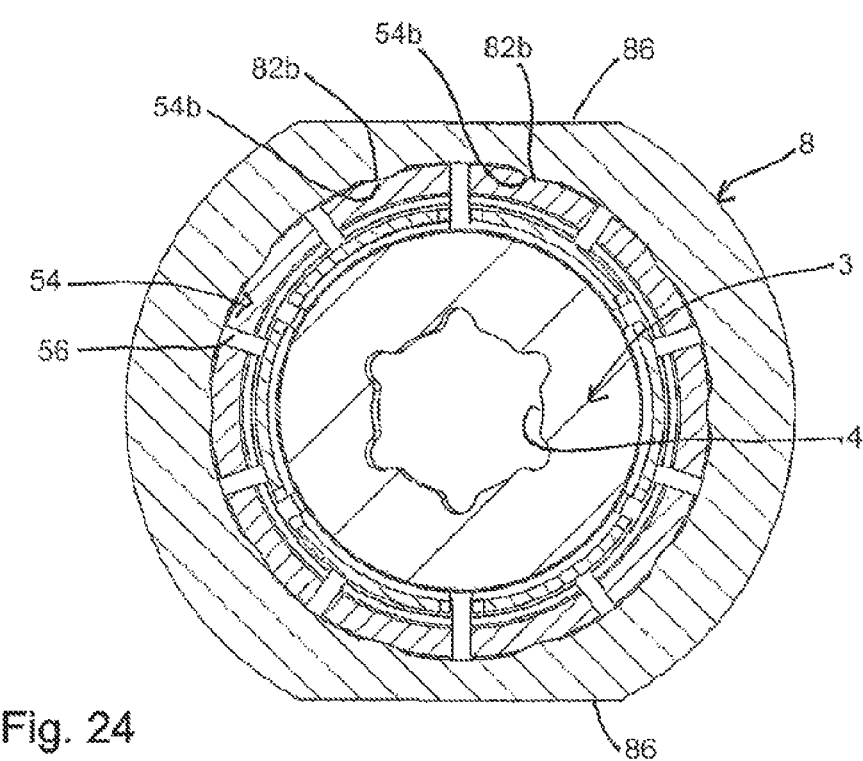
FIG. 24 shows an enlarged cross-sectional view of the polyaxial bone anchoring device of FIG. 23, the cross-section taken along line E-E in FIG. 23.

The size of the inner cylindrical surface 82 including the bulges 82b, is such that when the locking ring 8 is mounted around the head receiving portion 54 of the receiving part 5, the bulges 82b fit into the grooves 54b without compressing the flexible wall sections 54a of the head receiving portion 54 (see also FIG. 24). The locking ring 8 and the head receiving portion 54 are configured to cooperate in such a manner that rotating the locking ring 8 to some extent around the central axis C moves the bulges 82b out of the grooves 54b, thereby compressing the flexible wall portions 54a due to the bulges 82b pressing thereon.

The locking ring 8 may in addition have two opposite flat portions 86 at the outer spherical surface 81 on each side of the arms that are configured to be aligned with the rod channel when the locking ring 8 is mounted to the receiving part 5. A distance between the arms 83a, 83b in a circumferential direction is such that at least the rod can be placed between the arms. As shown, for example, in FIG. 2, a height of the arms 83a, 83b is such that the free end 84 of the arms is at a distance below the engagement recess 57 when the locking ring 8 is mounted to the receiving part 5.

The pressure member 7 will be described in more detail, referring additionally to FIGS. 13 to 16. The pressure member 7 includes an upper or first portion 71 with an upper end 7a and a lower or second portion 72 with a lower end 7b. The second portion 72 defines a hollow interior chamber 73 providing an opening at the second end 7b. The hollow chamber 73 is configured to accommodate and clamp the spherical head 3 therein. To achieve this, the second portion 72 is at least partially flexible by means of slits 74 that are open towards the second end 7b and end at a distance thereof, corresponding to an enlarged inner portion of the chamber 73. The slits 74 may have widened portions 74a at their closed ends. The number and dimensions of the slits 74 are such that the wall of the second portion is flexible enough to snap onto the head 3 when the head 3 is being inserted. An outer surface of the second portion 72 is substantially cylindrical with an outer diameter that allows the pressure member to slide through the passage 51 into the accommodation space 51b of the receiving part. A lower end portion 76 adjacent to the second end 7b is configured to cooperate with the narrowing portion 51c of the head receiving portion 54. For example, the lower end portion 76 may be tapered like the narrowing portion 51c of the receiving part.

The first portion 71 of the pressure member may also have a substantially cylindrical outer surface that is flush with the second portion 72. A rod support surface 77 configured to support an inserted rod 6 may be provided in the first portion 71. The rod support surface 77 may have a V-shaped cross-section that extends in a direction transverse to the central axis C to permit supporting of rods of different diameters. Alternatively, the rod support surface 77 may be flat or cylindrical or otherwise shaped.

To the left and to the right of the rod support surface 77, upstanding legs 78a, 78b are formed that have a substantially cylindrical outer surface. For example, the legs 78a, 78b may be manufactured by providing slots 79 to the left and to the right of the support surface 77. By means of the slots 79, the legs 78a, 78b can be bent inwards towards the rod support surface 77. Outwardly directed portions 700 are formed on the free ends of the upstanding legs 78a, 78b, respectively. The outwardly directed portions 700 are configured to engage the groove 58a in the passage 51 of the receiving part 5 when the pressure member 7 is in an insertion position, and to engage the groove 58b when the pressure member is in a pre-locking position.

At the center of the upstanding legs 78a, 78b, axially elongated through-holes 701 may be provided, the longitudinal axis of which is parallel to the central axis C when the pressure member 7 is inserted into the receiving part 5. The through-holes 701 are adapted to be engaged by the pins 509 or other holding means to hold the pressure member 7 inside the receiving part 5, and preferably to also secure the pressure member 7 against rotation. To allow access to the head 3 with a driver or a tool, a coaxial bore 702 may also be provided in the pressure member 7.

The dimensions of the pressure member are such that the flexible part of the second portion 72 can expand in the accommodation space 51b when the head 3 of the bone anchoring element 1 is being inserted.

Turning now to FIGS. 3, 4 and 17 to 22, the instrument adapted to be used with the polyaxial bone anchoring device will be described. The instrument includes an outer tube 100 and an inner tube 120 slideably arranged within the outer tube 100. In the figures, only front portions of the outer tube 100 and the inner tube 120 are shown. Each of the outer tube 100 and the inner tube 120 further includes a rear portion that may have any suitable shape, in particular, that may have any grip or handle portions to hold and/or move the outer tube 100 relative to the inner tube 120. Preferably, the outer tube 100 and the inner tube 120 are slideable with respect to each other in a guided manner, for example, by protrusions guided in recesses or slots. This guidance may be released to facilitate removal of the instrument from the polyaxial bone anchoring device.

Figure 3:
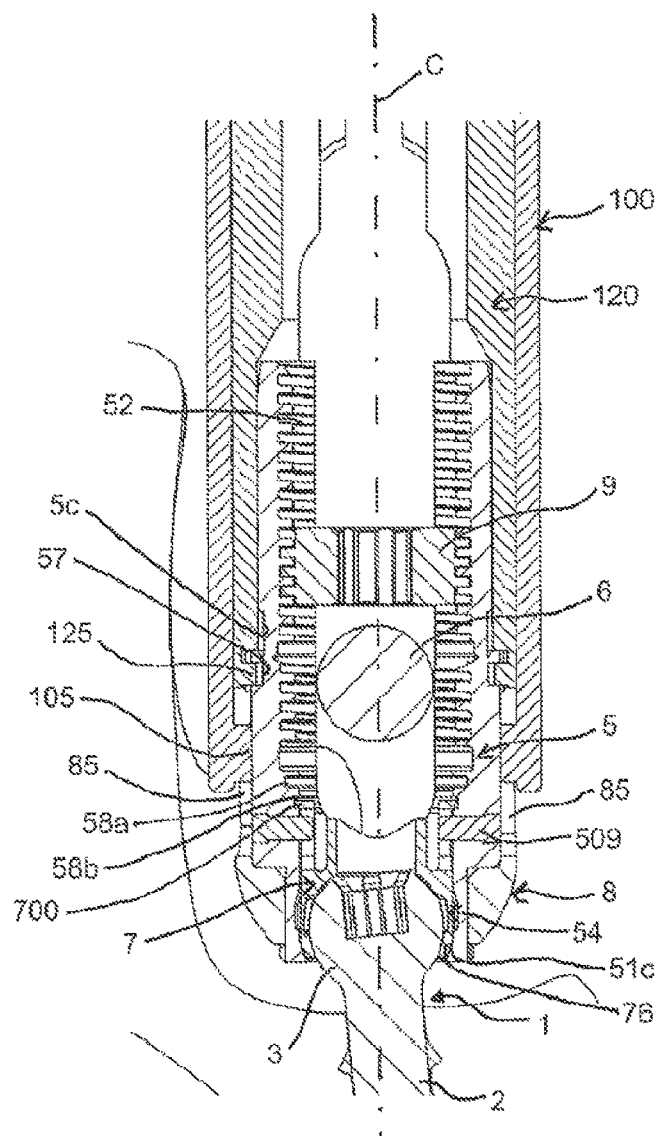
FIG. 3 shows a cross-sectional view of the polyaxial bone anchoring device of FIGS. 1 and 2 in an assembled state, together with a portion of an instrument, wherein the cross-section is taken in a plane perpendicular to the rod axis and extending through a central axis of the bone anchoring device.
Figure 4:
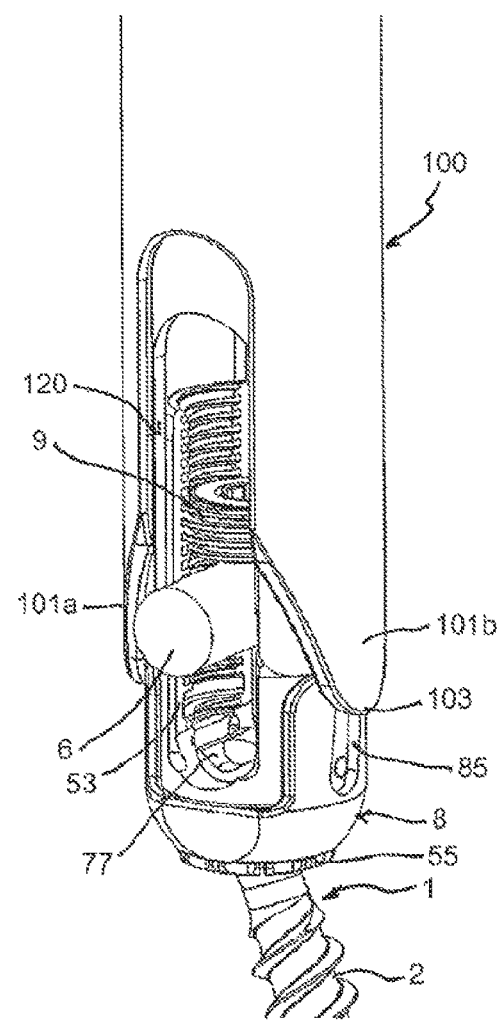
FIG. 4 shows another perspective view of the polyaxial bone anchoring device of FIGS. 1 to 3 in an assembled state.
Figure 9:
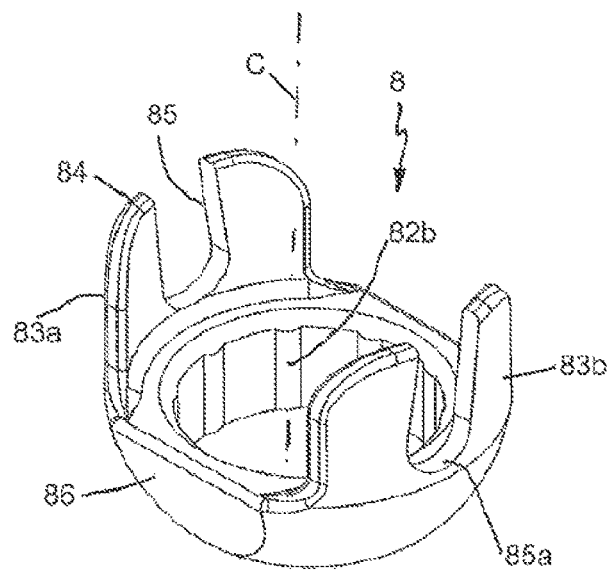
FIG. 9 shows a perspective view from a top of a locking ring of the polyaxial bone anchoring device of FIGS. 1 to 4.
Figure 10:
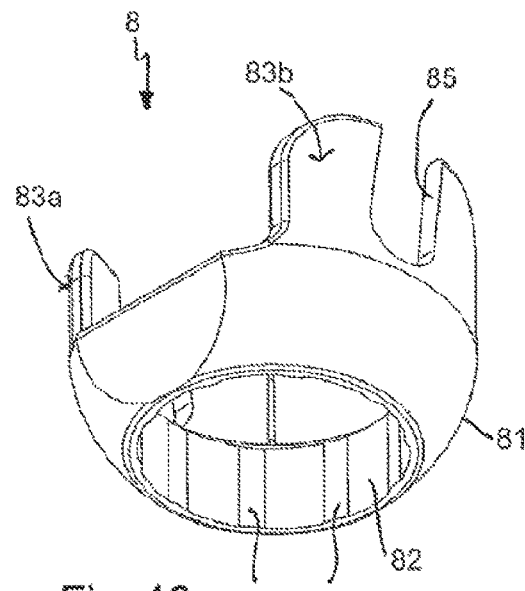
FIG. 10 shows a perspective view from a bottom of the locking ring of FIG. 9.
Figure 11:
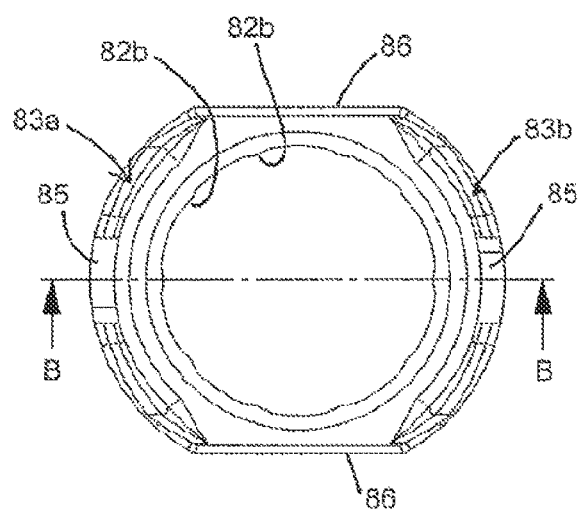
FIG. 11 shows a top view of the locking ring of FIGS. 9 and 10.

As shown in FIGS. 17 to 19, the outer tube 100 includes a front portion having two opposite arms 101a, 101b that are formed by a substantially U-shaped slot 102, wherein the open side of the slot is directed towards free ends 103. The substantially U-shaped slot 102 may continue at the bottom of the U-shape into a substantially rectangular slot 104 that is designed in such a manner that the front portion of the outer tube 100 has a sufficient flexibility to be placed over the upper part 50 of the receiving part 5, as shown in FIG. 3. The arms 101a, 101b may be substantially triangular shaped towards their free end 103. At or close to the free end 103, each arm 101a, 101b includes an inwardly directed protrusion 105 that fits into the notch 85 of the locking ring 8. The protrusion 105 is configured to be guided in the notch 85 in such a manner that a downward axial movement of the outer tube 100 leads to a pressure applied by the protrusion 105 onto the side wall of the notch 85, which causes a rotation of the locking ring around the central axis C.

The inner tube 120 includes a front portion having two arms 121a, 121b that are configured to engage the receiving part 5 and to hold the receiving part 5. The arms 121a, 121b are formed by a substantially U-shaped slot 122 that renders the arms 121a, 121b flexible to such an extent that they can snap onto the upper part 50 of the receiving part 5. More in detail, adjacent to a free end 123, the front portion has a substantially cylindrical recess 124 that is sized so as to accommodate the upper portion 530a, 530b of the legs 53a, 53b therein. Adjacent or close to the free end 123, inwardly projecting protrusions 125 are formed on each of the legs 121a, 121b that fit into the engagement recesses 57 at the receiving part 5. The cooperation between the protrusions 125 and the recesses 57 is such that the receiving part is held in a non-rotatable manner. As the receiving part 5 is coupled to the bone anchoring element 1, the inner tube 120 also fixes the receiving part 5 axially.

Figure 23:
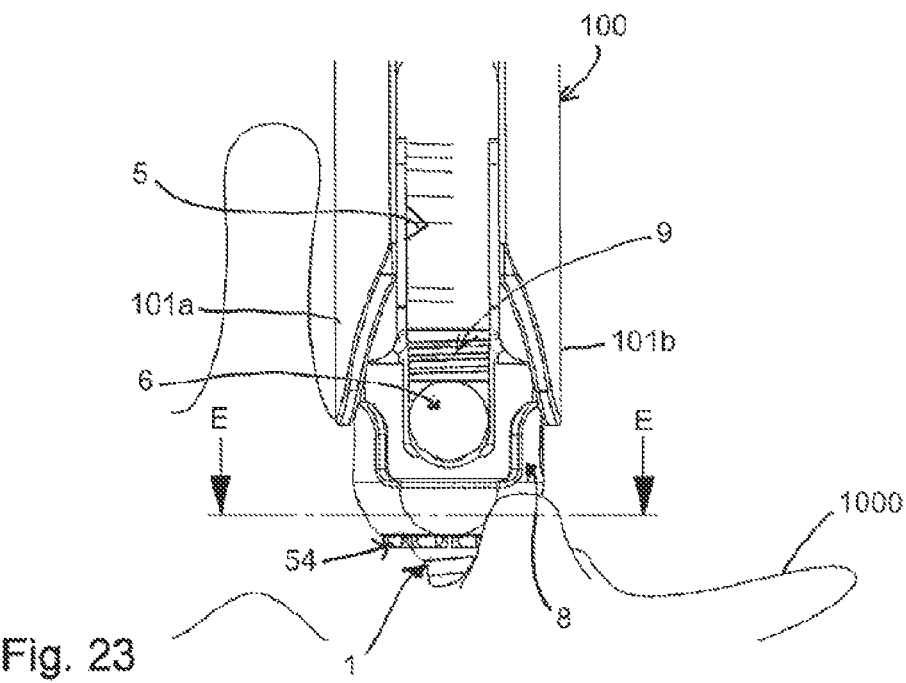
FIG. 23 shows a side view of the polyaxial bone anchoring device and a portion of the instrument, seen along the longitudinal axis of an inserted rod.

FIG. 23 shows the bone anchoring device with the anchoring element 1 inserted into a vertebra 1000 and with the outer tube arranged to cooperate with the notches 85 of the locking ring 8. FIG. 24 shows a cross-sectional view of the bone anchoring device, illustrating the engagement of the bulges 82b of the locking ring 8 and the grooves 54b of the head receiving portion as described above. This is the non-locking position of the locking ring 8.

The receiving part 5, the pressure member 7, the locking ring 8, and the bone anchoring element 1, as well as the rod 6 and the instrument, may each be made of bio-compatible materials, for example, of Titanium or stainless steel, of a bio-compatible alloy, such as NiTi-alloys, for example Nitinol, of magnesium or magnesium alloys, or of a bio-compatible plastic material, such as, for example, polyether ether ketone (PEEK) or poly-l-lactide acid (PLLA). In addition, the parts can be made of the same or of different materials from one another.

Turning now to FIGS. 25 to 33, the use of the polyaxial bone anchoring device and the instrument will be explained. First, as illustrated in FIGS. 25a and 25b, the bone anchoring element 1 and the pre-assembled receiving part 5 with pressure member 7 and locking ring 8 may be inserted into a bone, for example the pedicle of a vertebra 1000. This can be achieved as follows. In a first manner of use, the bone anchoring element 1 is first inserted into the bone. Then, the assembly of the receiving part 5, pressure member 7, and locking ring 8 is mounted onto the head 3 of the bone anchoring element 1. The pressure member 7 is held in the receiving part 5 by means of the pins 509 that engage the elongated through-holes 701 of the pressure member. By means of this, the rod support surface 77 is aligned with the channel 53 of the receiving part 5.

In the non-locking position of the locking ring 8, the head 3 of the bone anchoring element 1 can enter through the lower opening of the head receiving portion 54 into the accommodation space 51b, and more specifically, into the interior chamber 73 of the pressure member 7. When the head 3 enters into the head receiving portion 54, the pressure member 7 is moved upwards towards the first end 5a of the receiving part 5. This is the insertion position in which the pressure member 5 is in the uppermost position, and in which the outwardly extending portions 700 engage the groove 58a so that the pressure member 7 is prevented from escaping through the first end 5a of the receiving part (not shown in the drawing). The flexible second portion 72 of the pressure member 7 can expand in the accommodation space to permit the head 3 to enter.

In an alternative manner of inserting the bone anchoring device, the bone anchoring element 1 and the receiving part 5 with the pressure member 7 and the locking 8 are already pre-assembled prior to insertion into the bone.

Figure 25A:
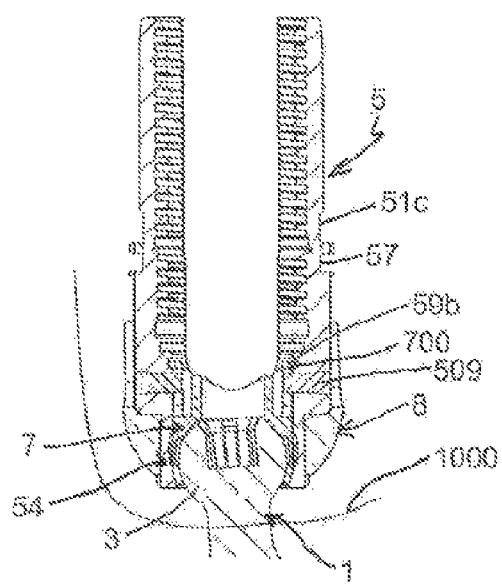
FIGS. 25a and 25b show a cross-sectional view and a perspective view, respectively, of the polyaxial bone anchoring device of FIGS. 1 to 4 inserted into a vertebra.
Figure 25B:
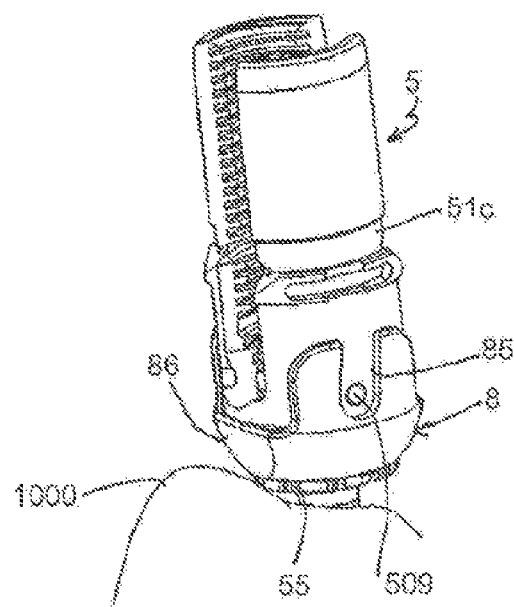

In the condition shown in FIGS. 25a and 25b, the pressure member 7 has been moved down so that the end portions 700 engage the groove 58b and the head 3 is prevented from moving through the lower opening (e.g., a pre-locking condition). The receiving part 5 is pivotable relative to the head 3, depending on the size of the head receiving portion 54 and the pressure member 7, any angular position of the bone anchoring element 1 relative to the receiving part 5 can be maintained based on the friction between the cooperating surfaces of the head 3 and the pressure member 7.

Figure 26:
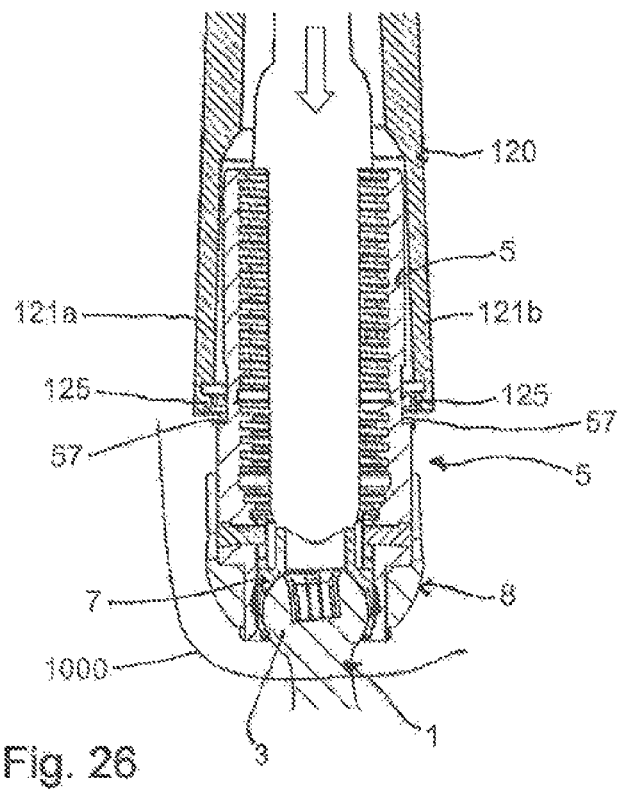
FIG. 26 shows a cross-sectional view of the polyaxial bone anchoring device of FIGS. 25a and 25b together with a portion of the inner tube of the instrument during a step of mounting the inner tube.

Next, as shown in FIG. 26, the inner tube 120 of the instrument is placed onto the receiving part 5 such that the arms 121a, 121b of the inner tube 120 are aligned with the legs 53a, 53b of the receiving part. The inner tube 120 is slid downward until the inwardly projecting protrusions 125 snap into the recesses 57 at the outer surface of the legs, as illustrated in FIGS. 27a and 27b. Thereby, the inner tube 120 and the receiving part 5 are fixed relative to each other with respect to translational and rotational movement.

Thereafter, as depicted in FIGS. 28a and 28b, the outer tube 100 is placed onto the inner tube 120 in such an orientation that the arms 101a, 101b are at a position of the U-shaped recess 53 of the receiving part 5. Hence, the protrusions 105 project into the rod channel. It shall be noted that markings or any other alignment or orientation features may be present at the inner and outer tube so that the outer tube can be placed correctly onto the receiving part.

Figure 29A:
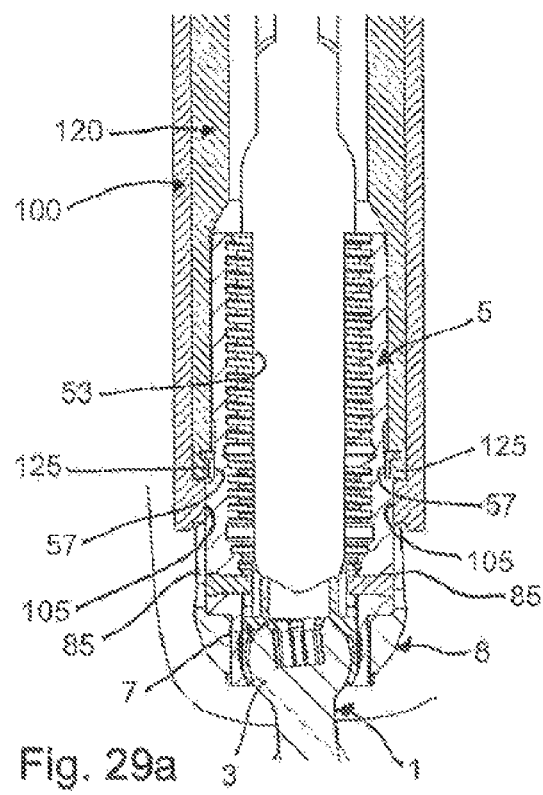
FIGS. 29a and 29b show a cross-sectional view and a perspective view, respectively, of the polyaxial bone anchoring device of FIGS. 28a and 28b, and after the outer tube is rotated by 90°.
Figure 29B:
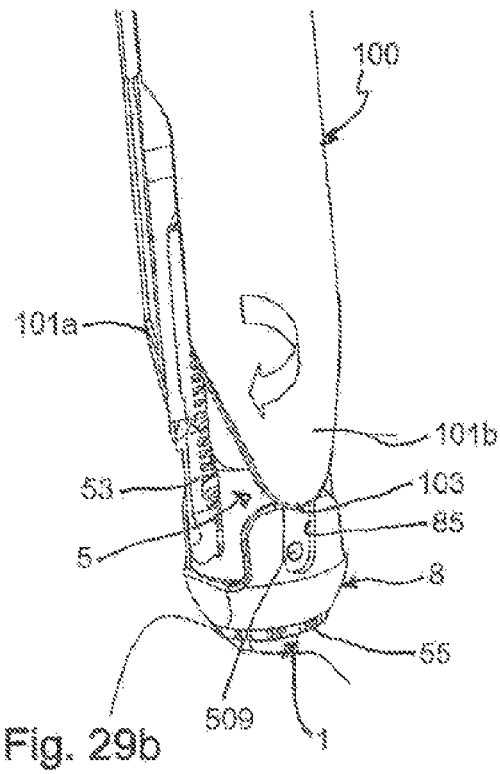

As shown in FIGS. 29a and 29b, the outer tube 100 is then rotated by 90° so that the protrusions 105 are located above the inclined notches 85 of the locking ring 8. Also in this case, the correct placement may be indicated and monitored at the rear ends of the instrument.

Figure 30A:
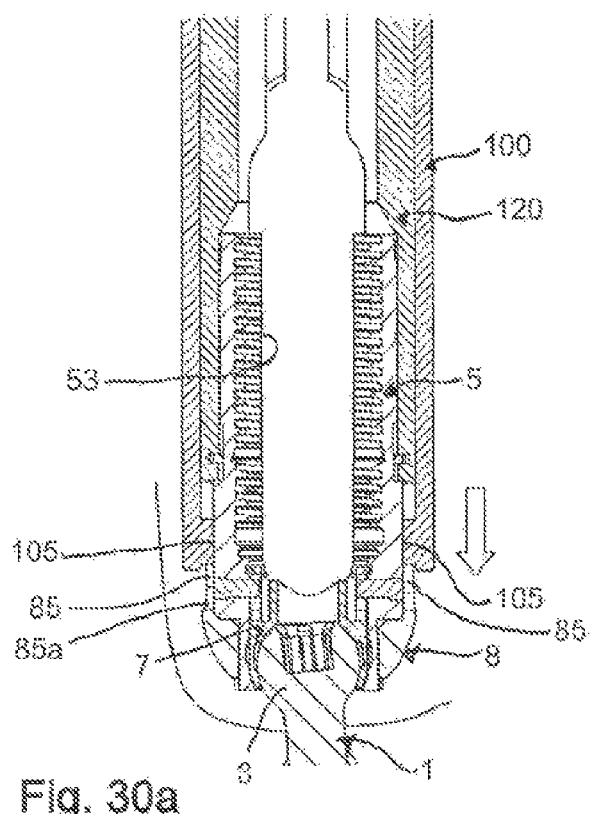
FIGS. 30a and 30b show a cross-sectional view and a perspective view, respectively, of the polyaxial bone anchoring device of FIGS. 29a and 29b, and after the outer tube is moved downward to a first distance.
Figure 30B:
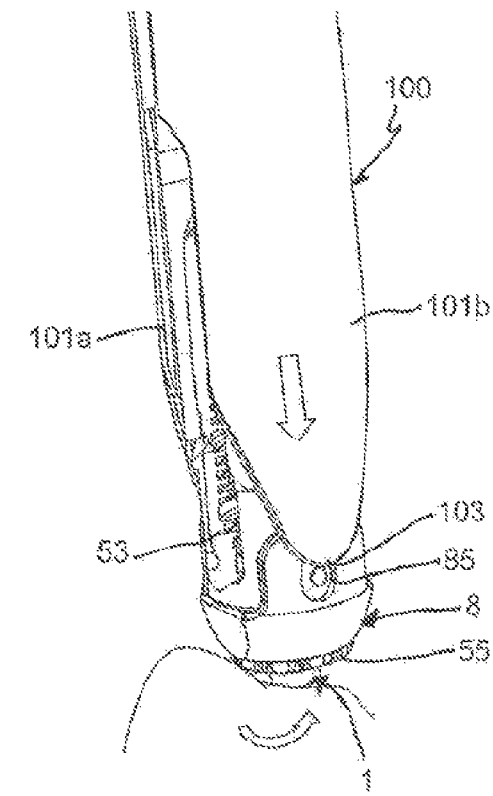

Next, as depicted in FIGS. 30a and 30b, the outer tube 120 is moved downward so that the protrusions 105 engage the inclined notches 85 of the locking ring 8, thereby rotating the locking ring in the direction indicated by the arrow in FIG. 30b. Hence, as the protrusions 105 are guided by the notches 85, the locking ring 8 follows the guidance and is rotated. While rotating, the bulges 82b of the locking ring move out of the grooves 54b of the head receiving portion and cause the flexible wall portions 54a to be compressed. Thereby, the polyaxial locking of the head 3 is effected.

Figure 31A:
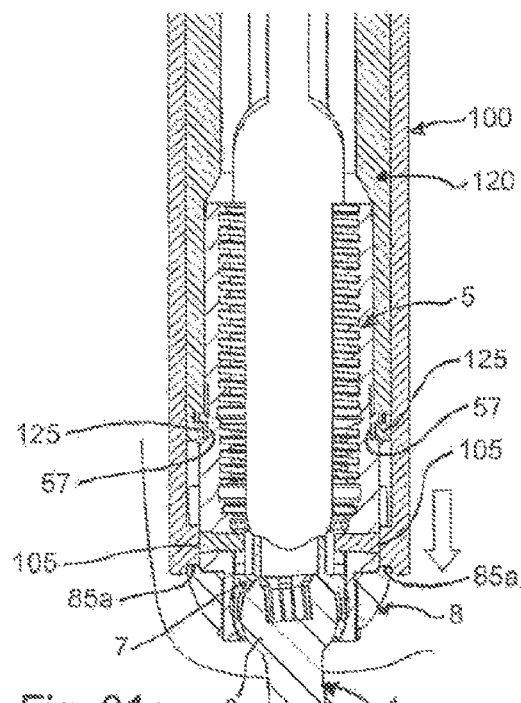
FIGS. 31a and 31b show a cross-sectional view and a perspective view, respectively, of the polyaxial bone anchoring device of FIGS. 30a and 30b, and after the outer tube is moved to a lowermost position.
Figure 31B:
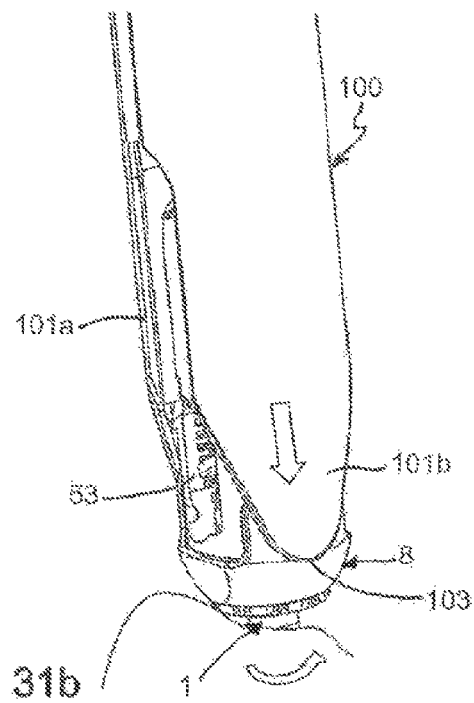

FIGS. 31a and 31b show the lowermost position of the outer tube 100 where the protrusions 105 are at the bottoms 85a of the inclined recesses or notches 85 of the locking ring 8. This corresponds to a locking position where the head 3 is locked in the head receiving portion 54. It shall be noted that during downward movement of the outer tube 100, the outer tube may be guided with respect to the inner tube 120 (not shown), so that a rotation of the outer tube relative to the inner tube may be prevented.

Figure 32:
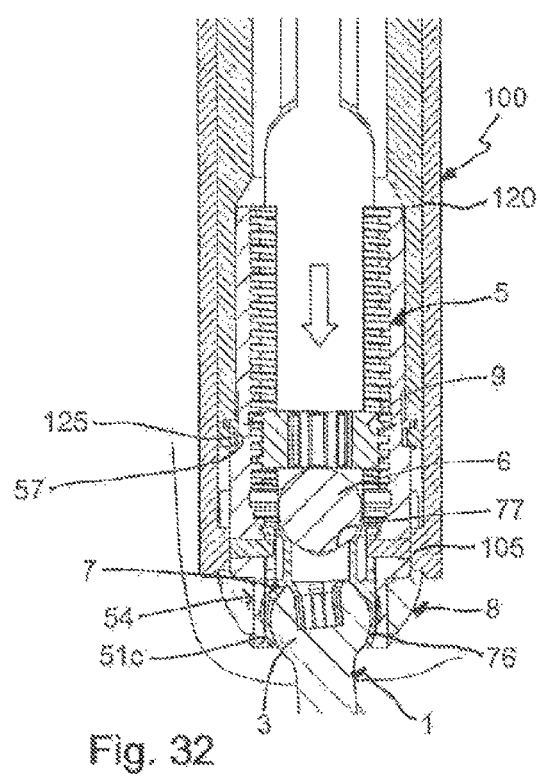
FIG. 32 shows a cross sectional view of the polyaxial bone anchoring device of FIG. 31a, and after the rod and the fixation screw are inserted.

Finally, as shown in FIG. 32, the rod 6 may be inserted, and after adjusting the position of the rod, it is fixed by the fixation screw 9. The fixation screw 9 also exerts pressure via the rod 6 onto the pressure member 7, whereby the head 3 and the rod 6 are finally locked.

Figure 33:
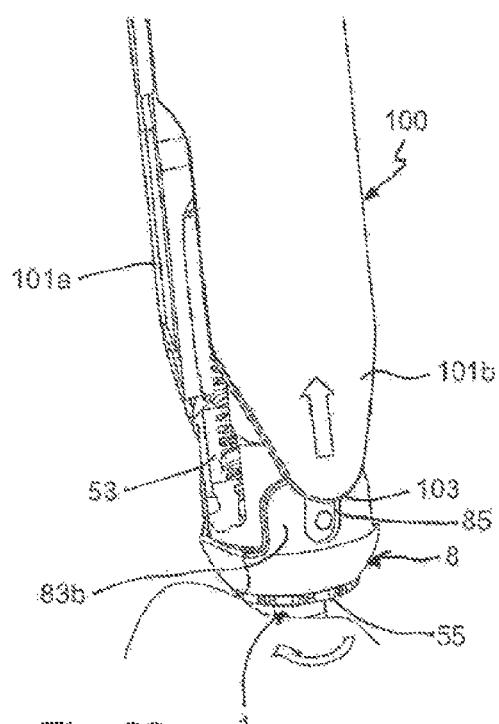
FIG. 33 shows a perspective view of the polyaxial bone anchoring device of FIG. 31b, and after the outer tube is moved upward.

FIG. 33 illustrates an operation of unlocking the head 3. The outer tube 100 is moved upward, whereby the locking ring 8 is rotated in the opposite direction as indicated by the arrow. Thus, the bulges 82b return to the grooves 54b of the head receiving portion 54, which defines an unlocking position of the locking ring 8.

In a surgical operation, first at least two bone anchoring elements 1 may be anchored, for example into adjacent vertebrae. Then, the receiving parts 5 are mounted thereon. Thereafter, the rod 6 is inserted. Once a correct angular position of the head 3 has been found, the head 3 can be locked by rotating the locking ring 8. Re-positioning of the rod 6 is possible without loosening the locking of the head 3. Due to the upper portions 530a, 530b of the legs, it is possible to perform correction steps of the rod position and/or the angular position of the head 3 when the rod is at an elevated position in the recess 53. All correction steps can be carried out while the rod and the fixation element are already placed into the receiving part.

Figure 34:
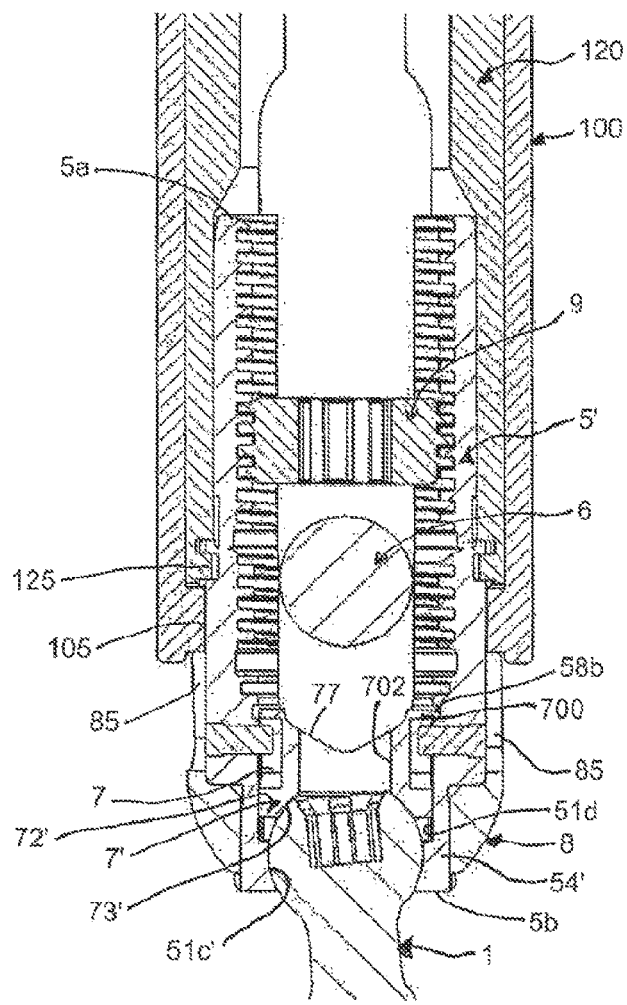
FIG. 34 shows a cross-sectional view of a further embodiment of a polyaxial bone anchoring device together with a portion of an instrument, wherein the cross-section is taken in a plane extending perpendicular to the longitudinal axis of an inserted rod and extending through a center of the receiving part.
Figure 35:
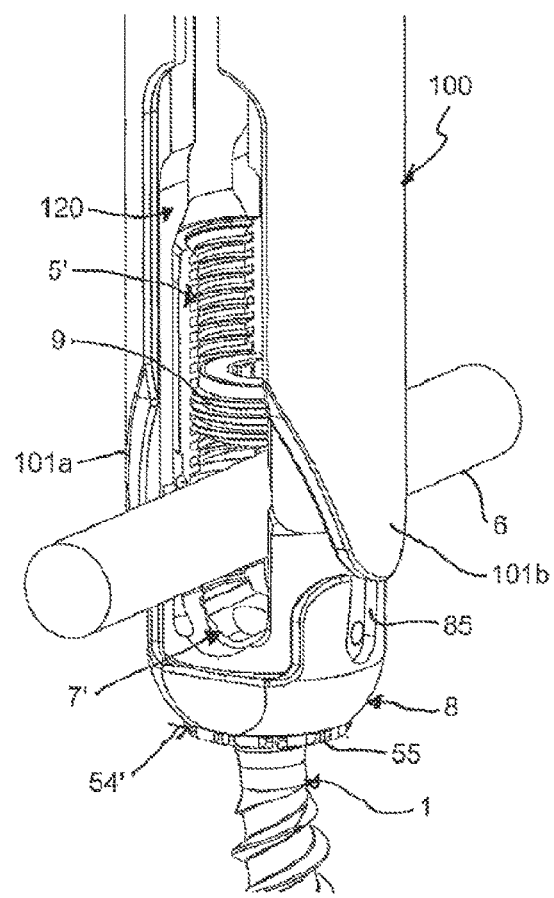
FIG. 35 shows a perspective view of the polyaxial bone anchoring device of FIG. 34.

A further embodiment of the polyaxial bone anchoring device will be described with respect to FIGS. 34 and 35. The embodiment according to FIGS. 34 and 35 differs from the previous embodiment in the design of the head receiving portion of the receiving part and in the design of the pressure member. All other parts are the same or similar to the previously described embodiments and are indicated with the same reference numerals as in the previous embodiments. The description thereof will not be repeated. The pressure member 7' lacks a flexible portion that encompasses the head 3 laterally. As shown in FIG. 34, the pressure member 7' has a second or lower portion 72' that is substantially cylindrical, and has at its lower side facing the head 3 a spherical recess 73' that accommodates an upper portion of the head 3. Hence, the pressure member 7' is configured to exert pressure onto the head 3 from above. The receiving part 5' includes a head receiving portion 54', wherein the accommodation space has adjacent to the lower end 5b a seat for the head 3, preferably a spherically-shaped hollow portion 51c' that simultaneously forms the narrowing portion and the seat.

When the locking ring 8 is rotated, the seat 51c' is pressed against the head 3 to clamp the head 3 temporarily, for example, during positioning and/or re-positioning of the rod. When the fixation screw 9 is finally tightened, pressure is exerted onto the pressure member 7' which in turn presses the head 3 into the seat 51c', whereby the head and the rod are locked.

Further modifications of the above-described embodiments may also be contemplated. For example, the invention is not restricted to rotating of the locking ring with the specific embodiments of engaging an inclined recess or notch of the locking ring with a protrusion of the instrument. It may be also possible to rotate the locking ring directly with an instrument.

Other engagement structures of the receiving part and/or the locking ring may also be contemplated that provide a connection between the instrument and the receiving part or the locking ring.

The bone anchoring device according to other embodiments of the invention can be provided in further modified forms. For example, the head of the bone anchoring element can have any other shape, such as, for example, a cylindrical shape or a spherical shape with flattened sides, wherein a monoplanar device is provided that allows pivoting of the anchoring element in a single plane. The head can also be conically shaped or otherwise shaped, with the internal hollow section of the head receiving portion adapted to the specific shape. In a further modification, the flexibility of the head receiving portion may be based on or facilitated by properties of the materials, for example, a plastic material may be used, and the slits in the head receiving portion may be fully or partly omitted.

In the pressure member, the upstanding legs may be omitted. Other structures may be provided that prevent the pressure member from escaping during insertion of the head. The pressure member may also be shaped such that it can be inserted from the lower end of the receiving part. The pressure member can also be omitted altogether. In such a case, the head can be locked solely by the action of the locking ring onto the head receiving portion. The rod can be clamped solely between the fixation screw and the bottom of the rod receiving channel.

In some embodiments, the head receiving portion can have an inclined open end or can be otherwise asymmetric to allow for a greater angulation of an inserted head in one direction.

The extended tabs on the receiving part can be omitted.

In addition, in some embodiments, other kinds of fixation elements can also be used, for example, non-threaded locking elements that have an alternative advancement structure. In addition, all kinds of bone anchoring elements can be used, such as, for example, nails or bone anchors with barbs.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
   a receiving part for coupling a rod to a bone anchoring element, the receiving part having a first end, a second end, and a central axis extending in a single straight line between the first end and the second end, the receiving part comprising:
      two legs defining a recess at the first end for receiving the rod; and
      a head receiving portion at the second end that is at least partially expandable and having an opening at the second end for inserting and pivotably holding a head of the bone anchoring element therein; and
   a locking ring mountable around the head receiving portion and movable axially relative to the receiving part in a direction parallel to the central axis, the locking ring comprising a tool engagement surface configured to be engaged by a tool for rotating the locking ring around the central axis to increase a compressive force exerted on the head receiving portion,
   wherein the tool engagement surface has at least a first portion that is spaced apart circumferentially from the recess for receiving the rod, and wherein the first portion faces the first end of the receiving part and is arranged at an incline relative to the central axis as the first portion extends circumferentially around the locking ring.

2. The bone anchoring device of claim 1, wherein the tool engagement surface is formed by a groove that is open towards the first end of the receiving part.

3. The bone anchoring device of claim 2, wherein the groove is open at a first end of the locking ring and extends towards a second end of the locking ring opposite the first end at an incline relative to the central axis.

4. The bone anchoring device of claim 1, wherein the tool engagement surface is formed on an arm that extends towards the first end of the receiving part.

5. The bone anchoring device of claim 4, wherein the arm comprises a first arm part and a second arm part circumferentially spaced apart from one another by the tool engagement surface.

6. The bone anchoring device of claim 5, wherein the tool engagement surface is configured to convert an axial force from a tool to a rotational force for rotating the locking ring relative to the central axis.

7. The bone anchoring device of claim 5, wherein the first arm part and the second arm part are configured to be positioned circumferentially between a first open end and a second open end of the recess for receiving the rod.

8. The bone anchoring device of claim 5, wherein the tool engagement surface is formed by a groove that extends into the arm at an incline relative to the central axis.

9. The bone anchoring device of claim 5, wherein at least part of the tool engagement surface is curved towards a second end of the locking ring opposite the first end of the locking ring.

10. A system comprising the bone anchoring device of claim 1, and a tool having a longitudinal axis and comprising an engagement portion engageable with the locking ring, wherein an axial displacement of the engagement portion of the tool results in a rotational movement of the locking ring.

11. The system of claim 10, wherein the tool further comprises:
   an inner portion; and
   an outer portion comprising the engagement portion, the outer portion being axially displaceable relative to the inner portion to axially displace the engagement portion relative to the inner portion to engage the tool engagement surface.

12. The system of claim 11, wherein, when the outer portion is axially displaced relative to the inner portion to engage the tool engagement surface, the inner portion is configured to engage the receiving part to hold the receiving part in a non-rotatable manner.

13. The system of claim 10, wherein:
   the tool engagement surface is formed by a groove on the locking ring that is open towards the first end of the receiving part; and
   the engagement portion comprises a protrusion configured to be received in the groove.

14. The system of claim 13, wherein, the first portion of the tool engagement surface is formed as an inclined surface in the groove, such that when the engagement portion is axially displaced, the inclined surface is configured to convert the axial displacement of the protrusion into the rotational movement of the locking ring.

15. A bone anchoring device comprising:
   a receiving part for coupling a rod to a bone anchoring element, the receiving part having a first end, a second end, and a central axis extending between the first end and the second end, the receiving part comprising:
      two legs defining a recess at the first end for receiving the rod; and
      a head receiving portion at the second end that is at least partially expandable and having an opening at the second end for inserting and pivotably holding a head of the bone anchoring element therein; and
   a locking ring that is mountable around the head receiving portion in an axial direction to a first axial position while the locking ring remains at a first rotational orientation relative to the receiving part, and that is further configured to be held at the first axial position while the locking ring remains at the first rotational orientation and while the locking ring remains substantially free from any forces from outside the bone anchoring device acting thereupon;

wherein a protrusion extends radially away from at least one of an outer surface of the head receiving portion or an inner surface of the locking ring as the surface extends circumferentially, such that when the locking ring is around the head receiving portion, the locking ring is rotatable around the central axis from a first rotational orientation to a second rotational orientation where the protrusion is engaged to increase a compressive force exerted by the locking ring on the head receiving portion compared to the first rotational orientation; and wherein each of the legs comprises a weakened portion that permits breaking away of part of the legs to shorten a height of the receiving part, and the legs comprise an internal thread for engaging a fixation element, the internal thread extending into the part of the legs configured to be broken away.

16. A bone anchoring device comprising:

a receiving part for coupling a rod to a bone anchoring element, the receiving part having a first end, a second end below the first end, and a central axis extending between the first end and the second end, the receiving part comprising:
two legs defining a recess at the first end for receiving the rod; and
a head receiving portion having an opening at the second end for inserting and pivotably holding a head of the bone anchoring element therein; and a pressure member positionable at least partially in the head receiving portion for exerting pressure on the head of the bone anchoring element when the head is received in the head receiving portion, the pressure member comprising:
a first portion defining a rod support surface configured to extend into the recess for receiving the rod to contact the rod; and
a second portion having a radially inwardly facing surface defining a chamber for holding the head, the radially inwardly facing surface having a first radius of curvature configured to contact the head and an enlarged region that deviates radially outwardly from the first radius of curvature and that separates portions of the radially inwardly facing surface having the first radius of curvature into an upper region above the enlarged region and a lower region below the enlarged region, such that a wall thickness of the second portion at the enlarged region is reduced compared to a wall thickness of the second portion where the radially inwardly facing surface has the first radius of curvature.

17. The bone anchoring device of claim 16, wherein the pressure member comprises a plurality of slits extending along the lower region and the enlarged region of the second portion.

18. The bone anchoring device of claim 17, wherein each of the plurality of slits has an open end at the lower region, and a closed end at the enlarged region.

19. The bone anchoring device of claim 18, wherein at least one of the plurality of slits has a widened portion at the closed end.

20. The bone anchoring device of claim 16, wherein the pressure member comprises a substantially cylindrical outer surface portion that extends at least from an axial position corresponding to the rod support surface to an axial position corresponding to the enlarged region.

* * * * *

UNITED STATES PATENT AND TRADEMARK OFFICE
CERTIFICATE OF CORRECTION

| | | |
|---|---|---|
| PATENT NO. | : 11,937,850 B2 | |
| APPLICATION NO. | : 17/190937 | |
| DATED | : March 26, 2024 | |
| INVENTOR(S) | : Timo Biedermann et al. | |

It is certified that error appears in the above-identified patent and that said Letters Patent is hereby corrected as shown below:

On the Title Page

In item (73), in Column 1, under "Assignee", Lines 1-2, delete "BIEDERMANN TECHNOLOGIES & CO. KG," and insert -- BIEDERMANN TECHNOLOGIES GMBH & CO. KG, --.

In the Specification

In Column 10, Line 38, delete "poly-I-lactide" and insert -- poly-l-lactide --.

Signed and Sealed this
Second Day of July, 2024

Katherine Kelly Vidal
*Director of the United States Patent and Trademark Office*